United States Patent [19]
Hawthorne et al.

[11] 4,062,883
[45] Dec. 13, 1977

[54] POLYMER-BOUND METALLOCARBORANE CATALYST PRODUCT AND PROCESS

[75] Inventors: M. Frederick Hawthorne; William Kalb, both of Los Angeles, Calif.

[73] Assignee: The United States of America as represented by the Secretary of the Navy, Washington, D.C.

[21] Appl. No.: 712,416

[22] Filed: Aug. 6, 1976

[51] Int. Cl.$^2$ .............................................. C07F 15/00
[52] U.S. Cl. .......................... 260/429 R; 252/431 R; 252/431 P; 260/683.2; 260/683.9; 560/234
[58] Field of Search ........................ 252/431 P, 431 R; 260/429 R, 2 M, 2 P

[56] References Cited
U.S. PATENT DOCUMENTS 3,900,557  8/1975  Strathdee .......................... 252/431 P
3,976,596  8/1976  Hawthorne ....................... 252/431 P

OTHER PUBLICATIONS

Journal of The American Chemical Soc.; vol. 96, No. 14 7/10/74, pp. 4674–4676; T. E. Paxson et al.
Journal of The American Chemical Soc.; vol. 96, No. 14 7/10/74, pp. 4676–4677; E.L. Hoel et al.

Primary Examiner—Winston A. Douglas
Assistant Examiner—P. E. Konopka
Attorney, Agent, or Firm—Richard S. Sciascia; Paul N. Critchlow

[57] ABSTRACT

A heterogeneous metallocarborane catalyst bound to a polymeric support by a carbon-boron bond. Chloromethylated polystyrene beads provide the support. The catalytic beads are characterized as 3,3-(Ph$_3$P)$_2$-3-H-4 polystyrylmethyl - 3,1,2-Rh C$_2$B$_9$H$_{10}$.

4 Claims, No Drawings

POLYMER-BOUND METALLOCARBORANE CATALYST PRODUCT AND PROCESS

BACKGROUND OF THE INVENTION

The present invention relates to the formulation of catalysts and in particular, to the binding of active catalytic molecules to polymeric supports.

The concept of binding active catalytic molecules to polymeric or other supports initially was developed by biochemists who used these systems for enzymatic purposes and as a method for conveniently separating or recovering the catalytic material from the reaction mixture. More recently, as will be described, these systems have been the object of a number of studies which, in particular, recognize the advantage gained by the inherent simplification and ease of the catalyst recovery and separation.

The polymer-bound catalysts of the present invention can be identified as heterogeneous systems as contrasted with the more common and increasingly important homogeneous catalytic systems. For the most part, however, the present systems are based upon the homogeneous systems. The distinction between the two lies principally in the fact that, in the homogeneous systems, the active catalytic material is only weakly associated with or deposited on its support material whereas, in the heterogeneous systems, the material is securely anchored by means of a strong chemical bond. Also, the homogeneous catalysts usually are soluble in the reaction mixture. In some situations, the distinction becomes difficult. However, insofar as the present invention is concerned, the term 'heterogeneous' is applied to polymer-bound systems in which the catalytic material is chemically bonded with sufficient strength to permit ready separation of the catalyzed product from catalytic material without appreciable catalyst loss or degradation of its activity. In the homogeneous systems, the dissociation and/or solubility of the catalytic material renders recovery of the material difficult and also presents a problem in separating the product itself. Consequently, redeposition of the material is required for recycling as opposed to the simplified filtering and recycling procedure provided by the heterogeneous catalysts.

Previous work by others has produced some interesting findings. For example, in the later 1960's several catalytic systems based upon homogeneous systems were described in the literature. One of the first extensively studied polymer bound homogeneous systems was that of the polystyrene-bound analog of Wilkinson's catalyst described in the following reports:

Grubbs, R. H., and Kroll, L. C., *J. Amer. Chem. Soc.* 93, 3062 (1971)

Grubbs, R. H. Kroll, L. C., and Sweet, E. J., *J. Macromol - Sci. Chem.* A7(5): (1973)

Wilkinson's catalyst was chosen because of a great deal of work that had been published on its catalytic reaction mechanisms. It was found that the complex appeared to function in the polymer bead as it would in solution for the hydrogenation of olefins. However, the activity was decreased by the binding with the lowered activity attributed to the slow diffusion of the olefin through the polystyrene matrix. This property, however, allowed a good deal of selectivity on the part of the catalyst and the catalyst was easily separated and recycled.

Similar studies were conducted with $RhH(CO)(PPh_3)_3$ in hydroformylation reactions. This polymer-bound catalyst retained catalytic activity through several successive reaction-separation-reaction cycles and no loss of rhodium was observed. See:

Collman, J. P., et al., *J. Amer. Chem. Soc.*, 94, 1789 (1972)

Pittman, C. U. and Hanes, R. "Frontiers in Organometallic Chemistry" Ann, NY Acad. Sci., 239, 76 (1974)

Evans, D. Osborn, J. A. and Wilkinson, G., and *J. Chem. Soc* (A), 3133 (1968)

A variety of polymer-attached transition metal catalytic systems also have been synthesized and reported in the following publications:

Pittman, C. U., Smith, L. R., and Hanes, R. *J. Amer. Chem. Soc.* 97, 1742 (1975)

Allum, K. G., Hancock, R. D., Howell, I.V. Pitkethly, R. C. and Robinson, P. J., *J. Organometal Chem.*, 87 189 (1975)

Allum, K. G., Hancock, R. D., Howell, I.V., McKenzie, S. Pitkethly, R. C. Robinson, P. J. *Organometal, Chem.* 87, 203 (1975)

These systems appear to be analogous in behavior to the homogeneous catalysts from which they were derived.

Besides varying the active complex, the polymeric support also can be designed to provide desired properties and a wide range of supports have been utilized. The two Organometal Chem. publications cited supra provide examples of this work.

As far as is known, polymer-bound metallocarborane catalyst systems have not been synthesized and described in the literature. Some systems have combined a polymer and carborane but the chemical attachment was through a phosphine-to-metal bond rather than through the direct bonding of the metallocarborane to the polymer which characterizes the present invention. In the reactions the phosphine-to-metal bond breaks down with the result that some metal catalyst is lost in the mixture so that the recovered catalyst loses some of its activity.

DETAILED DESCRIPTION OF THE PRESENT INVENTION

The present invention is predicated upon the discovery and synthesis of the first polymer-bound metallocarborane which is characterized as 3,3-$(Ph_3P)_2$-3-H-4 polystyrylmethyl-3,1,2-Rh$C_2B_9H_{10}$. Subsequent studies have shown that this polymer-bound rhodacarborane is an active heterogeneous catalyst for the hydrogenation and isomerization of olefins. As will be discussed, these results strongly indicate that a wide variety of heterogeneous catalysts conforming to the general composition of (polymer + carborane + metal) may be available through an extension of the synthetic routes that have been established.

A model system for the present discovery was provided when a series of boron-substituted derivatives of 7,8-$C_2B_9H_{12}^-$ was extended to include the benzyl substituent 9 benzyl-7,8-$C_2B_9H_{11}^-$ (which, for descriptive purposes, will be referred to as Compound I. The point of substitution is the 9-boron atom a polyhedral vertex adjacent to carbon and on the open face of the anion. Compound I reacted cleanly with $Rh(Ph_3P)_3Cl$ to give the rhodacarborane 3,3-$(ph_3P)_2$-3-H-4 benzyl 3,1,2-Rh $C_2B_9H_{10}$ (Compound II) in greater than 90% yield.

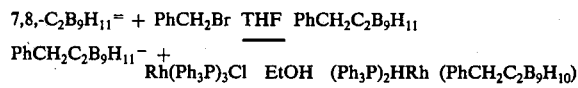

Subsequent experiments shows that benzene solutions of compound II catalyzed the hydrogenation of olefins such as ethyl acrylate and 3-methyl-3 phenylbutene-1 at a rate comparable to other hydridorhodacarboranes discussed in a manuscript prepared by J. J. Wilezynski and soon to be published.

The above results indicated that $7,8\text{-}C_2B_9H_{11}{}^{2-}$ could be reacted with chloromethylated polystyrene beads to form the polymer-bound anion analogous to compound II.

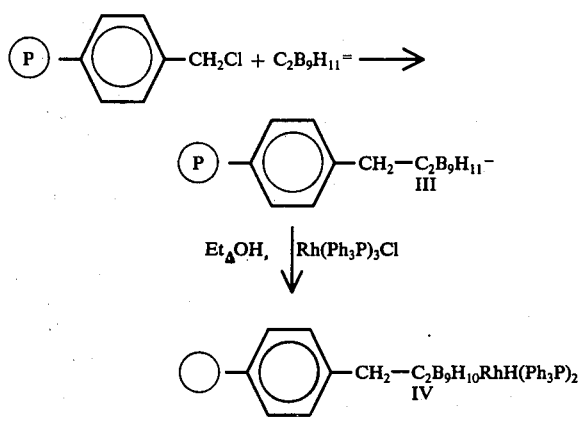

Chloromethylated polystyrene beads known in the art as Merrifield's Peptide Resin were reacted with an excess of $K^+$, $Na^+$-$7,8\text{-}C_2B_9H_{11}{}^=$ in refluxing THF. Dibenzo-18-crown-6 was used as a catalyst to aid in the transfer of the dianion into the lipophilic polymer. Filtration and washing afforded colorless beads (compound III above) which, on the basis of spectral and elemental analysis (coupled with the characterization data for Compound I) were formulated as $M^+$(9-polystyrylmethyl-7,8-$C_2B_9H_{11}$-), or Compound III.

The reaction of Compound III with an excess of $Rh(Ph_3P)_3Cl$ in refluxing ethanol yielded bright yellow beads (Compound IV above) which subsequently were characterized as 3,3-$(Ph_3P)_2$-3-H-4-polystyrylmethyl-3,1,2-$RhC_2B_9H_{10}$.

The beads (IV) - an amount equivalent to $10^{-4}$ in catalyst - in benzene solution rapidly isomerized 1-octene (0.3M). Within 24 hours at 40 degrees the reaction mixture contained 1-octane (14%), trans - 2 octene (65%) and cis-2-octene (20%).

Under a hydrogen atmosphere (1atm) IV ($10^{-4}$M) at 40° in benzene catalyzed the hydrogenation of 3-methyl-3-phenyl-1-butene ($10^{-1}$M) at a rate comparable to 11 and other hydridorhodocarboranes.

Although the polystyrene bead metallocarborane catalyst represents the present stage of development of the catalytic route which has been described, it clearly is recognized that a number of extensions of this route simply await application of a substantial amount of carborene derivative chemistry that is in existence and to some extent discussed in the publications that have been cited. For example, it is felt that the extension of this route to include other metallocarborane catalysts of the $C_2B_9H_{11}{}^{2-}$ family, as well as other cage homoloques is most promising. Also, the route can be extended to further generalize the method of polymer attachment through the carbon-boron bond to include other homoloques in this carborane and carborane anion series.

Another important approach presently being investigated is one of securing and utilizing derivatives of the carborane anions which, in themselves, can serve as monomers for polymerization. Thus, as has been discussed, the present stage of development involves condensation with a preformed polymer backbone, i.e., polystyrene beads.

However, polymerization itself, as contrasted with the use of the preformed beads, should have definite advantages some of which would include: (1) effective catalyst concentration (on the polymer) could be greatly increased and controlled by homopolymerization or copolymerization of monomer molecular catalyst precursors; (2) chiral monomers could be polymerized to provide macro-molecular catalysts whose catalytic sites are optically active and ideally suited for asymmetric reactions; (3) the techniques of polymer processing could be applied to yield catalysts whose physical characteristics are best suited to their use as heterogeneous catalysts.

The synthesis of one likely candidate for polymerization is the 9-vinylbenzyl derivatives of $C_2B_9H_{12}{}^-$. The following illustrates the path that is being pursued:

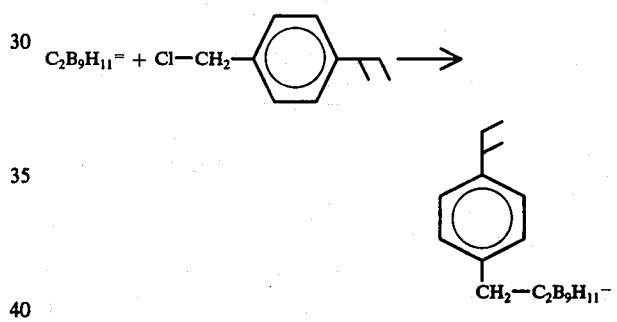

The reaction is strictly analogous to that which has been successfully demonstrated for 9-benzyl-7,8-$C_2B_9H_{11}{}^-$. It should be noted that such a monomer would exist as a set of enantiomers in that the 9-boron atom represents a point of asymmetric cage substitution. As such, optical resolution by fractional crystallization with an optically active cation would lead to a chiral and polymerizable carborane monomer.

Homopolymerization in solution or suspension polymerization with varying degrees of cross linking and/or other monomers then could be engineered to produce polymeric catalyst precursors with the desired characteristics. Conversion to a catalyst then can be achieved in the demonstrated manner. This scheme can be applied, as noted, to the optically active monomer to give chiral polymeric catalysts suited for asymmetric induction reactions.

The polymeric catalyst precursor would be ideal for the synthesis of multifunctional catalyst systems by stoichiometric control of metal reagents. In such a manner a heterogeneous catalysts adaptable to a "one-pot" multistep synthesis could be obtained. Proposals such as these, as well as other approaches, as likely candidates for the extensions of the presently-disclosed field.

Obviously, many modifications and variations of the present invention are possible in the light of the above teachings. It is therefore to be understood that within the scope of the appended claims the invention may be practiced otherwise than as specifically described.

We claim:

1. A heterogeneous catalyst for the hydrogenation and isomerization of olefins, said catalyst consisting of:
   the polymer-bound rhodacarborane 3-3-$(Ph_3P)_2$-3-H-4 polystyryl methyl-3,1,2-Rh $C_2B_9H_{10}$.

2. A method of forming a polymer-bound heterogeneous rhodacarborane catalyst for the hydrogenation and isomerization of olefins comprising:
   reacting preformed polystyrene beads with $C_2B_9H_{11}^-$ to obtain a bead-like product, and reacting said product with a rhodium compound to obtain said polymer-bound rhodacarborane as a final product,
   the general composition of said final product being a metallocarborane directly bound to said preformed bead.

3. The method of claim 2 wherein said beads are chloromethylated polystyrene beads and said rhodium compound is $Rh(Ph_3P)Cl$.

4. The method of claim 3 wherein said final product is 3-3-$(Ph_3P)_2$-3-H-4 polystyryl methyl-3,1,2-Rh $C_2B_9H_{10}$.